United States Patent [19]

Ogura et al.

[11] Patent Number: 4,769,231
[45] Date of Patent: Sep. 6, 1988

[54] HAIR TONIC COMPOSITION

[75] Inventors: Kyoichi Ogura; Takaharu Tanaka; Teruo Amachi; Hajime Yoshizumi, all of Mishima; Hideoki Ogawa, Tokorozawa, all of Japan

[73] Assignees: Suntory Limited, Osaka; Hideoki Ogawa, Tokorozawa, both of Japan

[21] Appl. No.: 853,859

[22] Filed: Apr. 21, 1986

[30] Foreign Application Priority Data

Apr. 23, 1985 [JP] Japan .................................. 60-85347

[51] Int. Cl.⁴ ................................................ A61K 7/06
[52] U.S. Cl. .................................... 424/74; 424/195.1
[58] Field of Search ........................ 424/70, 74, 195.1

[56] References Cited

FOREIGN PATENT DOCUMENTS 200458 11/1986 European Pat. Off. .
3442961 8/1985 Fed. Rep. of Germany ........ 424/70
2425241 1/1980 France ................................. 424/70
2530464 1/1984 France ................................. 424/70

OTHER PUBLICATIONS

Biological Abstracts 82086029, Effect of Plant Worm Extract on Mouse Hair Growth, Ogawa H, et al.
Shin Tei Wakan Yaku (Japanese and Chinese Medicine).

Primary Examiner—John E. Kittle
Assistant Examiner—Susan S. Rucker
Attorney, Agent, or Firm—Burns, Doane, Swecker & Mathis

[57] ABSTRACT

A hair tonic composition comprising an effective amount of an extract extracted by a solvent from dong chong xia cao and a conventional base medum for a hair tonic composition, a process for production thereof, and the use thereof.

6 Claims, 4 Drawing Sheets

HAIR TONIC COMPOSITION

BACKGROUND OF THE INVENTION

1. Field of the Invention

The present invention relates to a novel hair tonic composition suitable for use in preventing the generation of dandruff (or scurf) in hair and itching in the scalp and in accelerating the growth of hair. More specifically, it relates to a novel hair tonic composition containing, as an effective ingredient, an extract from dong chong xia cao.

2. Description of the Related Art

The possession of a healthy and profuse head of hair throughout life is the ambition of most human beings. Various kinds of hair dressings, including hair tonic compositions, have been used for alleviating or curing epilation or depilation (i.e., the involuntary loss of hair and subsequent balding). However, at present, there are no truly effective agents for alleviating epilation, accelerating the growth of hair, and further alleviating or curing the generation of dandruff in the hair and itching in the scalp.

The dong chong xia cao, which is a raw material for the hair tonic composition of the present invention, has been long known as a raw material for Chinese medicines. Dong chong xia cao was first described by Wu Iluo during the Ching dynasty in his book, *Ben Cao Cong Xin* (*Herbs from Anew*). After that it was described, for example, in Chinese publications *Zhong Yao Dacidian* (*Encyclopedia of Chinese Medicine*), and *Zhong Cao Yaoxue* (*Chinese Herbal Medicine*) and Japanese publications, *Shin Tei Wakan Yaku* (*Japanese and Chinese Medicine,* New Ed.) by Kinpo Akamastu, and a large number of other publications relating to Chinese medicines. These publications disclose various kinds of pharmacological effects provided by dong chong xia cao, and various prescriptions for the use of dong chong xia cao in Chinese medicines.

However, most Chinese medicines derived from the dong chong xia cao are orally administered, and it has not been known that an extract from dong chong xia cao will have an effect on the growth of hair through external application.

SUMMARY OF THE INVENTION

Accordingly, an object of the present invention is to provide a novel hair tonic composition comprising an effective amount of an extract extracted by a solvent from dong chong xia cao and a conventional base medium for a hair tonic composition, and the use thereof.

Moreover, the present invention provides a process for production of the hair tonic composition comprising extracting dong chong xia cao to obtain an extract, and optionally after evaporating the extract to dryness, combining the extract with a conventional base medium for a hair tonic composition.

DESCRIPTION OF THE PREFERRED EMBODIMENTS

Figure 1A:
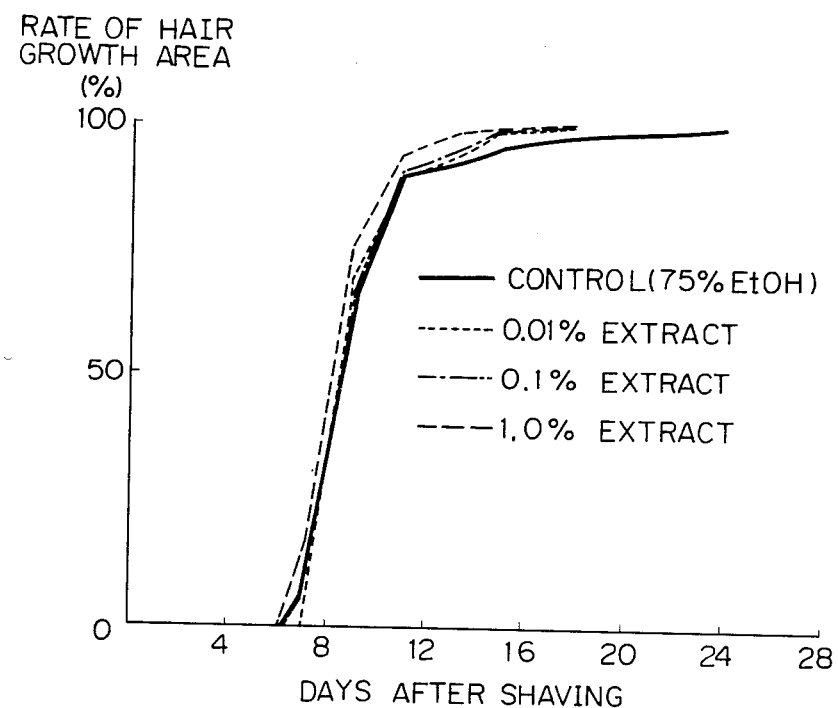
FIGS. 1 A and B are graphs showing the relationship between a hair-growth effect represented by an area of the skin of mice wherein hair is regenerated after shaving, and an amount of an extract from the dong chong xia cao contained in samples applied on the shaved skin; and, FIGS. 2 A and B are graphs showing the relationship between the hair-growth effect obtained as in FIG. 1 and a concentration of ethanol in a solvent used for extraction of dong chong xia cao.

Dong chong xia cao is a fruit body (fructification) of *Cordyceps sinensis* (Berk) Sacc generated from the larvae of *Hepialus armoricanus* infected with the fungi. The fruit body of the fungi and the host infected is usually dried to produce the product "dong chong xia cao", which is commercially available from China.

The term "extract from dong chong xia cao" as an ingredient of the present composition means materials transferred from the dong chong xia cao to a solvent used for the extraction, which may be present as dried matter or contained in the solvent used for the extraction. In the latter case, the solvent forms a part of the base material of the present hair tonic composition.

The solvents include water; alcohols, such as methanol, ethanol, and butanol; ethers, such as ethyl ether and dioxane; and ketone, such as acetone. When the extract is used after it is once prepared as a dry matter, any solvent listed above or any mixture thereof can be used. On the other hand, when the extract is used as a solution in the solvent, a solvent not harmful to the human body, such as water, ethanol, or a mixture thereof, should be used.

The dong chong xia cao may be subjected to the above-mentioned extraction in the intact form, or crushed prior to the extraction to accelerate the contact between dong chong xia cao and the solvent.

Although the ratio of the dong chong xia cao and the solvent during the extraction is not critical, preferably the ratio is 0.1 to 5 l of a solvent per 100 g of the dong chong xia cao. A temperature during the extraction is preferably between a room temperature and a boiling temperature of the solvent used. The term for the extraction is preferably 24 hours to two weeks, depending on the extraction temperature, etc. Preferably, the extraction is carried out at room temperature for several days with occasional stirring. It has been already confirmed in the field of Chinese medicine that the dong chong xia cao is not toxic to the human body. Therefore, the concentration of the extract as an ingredient in the hair tonic composition can be over a wide range. To obtain the target effects, and taking into consideration the cost of dong chong xia cao, a 0.00001 to 30% by weight (dry weight) of the extract in relation to the composition is preferably used.

The base materials used in the hair tonic compositions according to the present invention can include those conventionally used in any cosmetic compositions. Examples of such base materials which can be used in the present invention are distilled water; monohydric alcohols such as ethyl alcohol; polyhydric alcohols such as glycerine and ethylene glycol; fats and oils; surfactants.

In addition to the above-mentioned active ingredients, various conventional ingredients suitably used in the formulation of a hair tonic composition or a hair dressing composition can be incorporated in a conventional amount into the hair tonic composition of the present invention. Typical examples of such ingredients are hormones, vitamins, amino acids, herb extracts, photosensitizing dyes, resorcinol, menthol, wetting agents, and perfumes. These ingredients can be optionally incorporated into the hair tonic composition of the present invention unless the desired effect of the present invention is impaired.

When the hair tonic composition of the present invention is applied to a human scalp or an animal skin, it exhibits a strong hair growth effect. That is, when the composition is applied to a human scalp, depilation is inhibited, and hair which has become downy hair again becomes healthy hair, and the rate of hair growth is remarkably increased. Moreover, the generation of dandruff (or scurf) in the hair and itching in the scalp is alleviated. When the composition of the present invention is applied to the skin of an animal, the rate of hair growth is remarkably increased.

As mentioned above, dong chong xia cao has been administrated orally for a long time, and it has been confirmed that it is not toxic to humans or animals. For reconfirmation of this, 50 g of dong chong xia cao was soaked in 0.5 l of 75% ethanol for two days, and heated at boiling point for 5 hours to obtain an extraction. The extract was concentrated to dryness, and the residue thus obtained was dissolved in 50 ml of 75% ethanol. The solution was applied to the shaved skin of five rabbits, twice a day for 7 days. The results were compared with those obtained by a control, i.e., rabbits to which only a base material, 75% ethanol was applied. No abnormality was observed in the five rabbits to which the solution was applied.

EXAMPLES

The present invention will now be further illustrated by, but is by no means limited to, the following examples, in which the preparation, application, and effect of the hair tonic composition of the present invention are specifically disclosed.

EXAMPLE 1

PREPARATION OF EXTRACT (1) 50 g of dong chong xia cao was soaked in 500 ml of 75% ethanol at room temperature for ten days, and the mixture then filtered to obtain 480 ml of a yellowish brown extract solution.

(2) 50 g of dong chong xia cao was soaked in 500 ml of 70% ethanol at a room temperature for ten days, the mixture was then filtered to obtain a filtrate, which was then concentrated to dryness to obtain 13.2 g of a brown extract.

EXAMPLE 2

COMPOSITION

| Ingredient | Content (% by volume) |
| --- | --- |
| (1) Hair tonic | |
| 95% ethanol | 75 |
| Dong chong xia cao extract from Ex. 1(1) | 5 |
| propylene glycol | 0.2 |
| Menthol | 0.1 |
| Perfume (Alexander, ZE-8000 Takasago Koryo Co. Ltd.) | 0.5 |
| Distilled water | to 100 |
| (2) Hair Cream | |
| Liquid paraffin | 40 |
| Beeswax | 5 |
| Lanolin | 3 |
| Vaseline | 5 |
| Emulsifier (polyoxyethylene sorbitan sequiableate) | 2 |
| Propylene glycol | 1 |
| Dong chong xia cao extract from Exp. 1(2) | 3 |
| Perfume (Alexander, ZE-8000 Takasago Koryo Co. Ltd.) | 1 |
| Distilled water | to 100 |
| (3) Pomade | |
| Castor oil | 85 |
| Japanese wax | 10 |
| Dong chong xia cao extract from Exp. 1(2) | 3 |
| Perfume (Alexander, ZE-8000 Takasago Koryo Co. Ltd.) | 2 |

EXAMPLE 3

A hair tonic composition prepared according to Example 2(1) was applied to the scalps of 10 human males of between 29 to 60 years old, each suffering from dandruff, itching in the scalp and depilation, in an amount of 2 to 4 ml, once or twice a day for three months. The following results were obtained.

TABLE

| Subject | Age | Effect Dandruff | Itching | Depilation |
| --- | --- | --- | --- | --- |
| A | 60 | / | good | good |
| B | 50 | good | good | good |
| C | 44 | good | good | good |
| D | 36 | / | good | excellent |
| E | 34 | good | none | excellent |
| F | 32 | good | good | good |
| G | 41 | excellent | none | none |
| H | 38 | good | none | / |
| I | 29 | none | / | none |
| J | 41 | none | good | good |

EXAMPLE 4

TEST ON MICE

Male $C_3H$/HeNCrj mice(58 days old), were used in the following experiment carried out according to a method of Ogawa et al, *Normal and Abnormal Epidermal Differentiation,* ed. dy M. Seiji and I. A. Bernstein, Tokyo University press. An area of about 2×4 cm of the hair of each mouse was shaved, and from the day after shaving, a sample prepared as described below was applied to the shaved area once a day. The ratio of an area which changed from pink to gray in relation to the overall shaved area was measured. The change in color denoted the beginning of a regrowth of hair. The experiment was continued until all of the shaved areas of all of the mice were changed to gray.

For preparation of the samples, 30 g of ground dong chang xia cao was soaked in 400 ml of 75% ethanol for 7 days, and the mixture was filtered to obtain an original extract. Portions of the original extract were diluted with 75% aqueous ethanol to 10%, 1%, 0.1%, and 0.01%, taking the original extract as 100%. As a control, 75% aqueous ethanol was applied instead of the above sample.

Figure 1B:
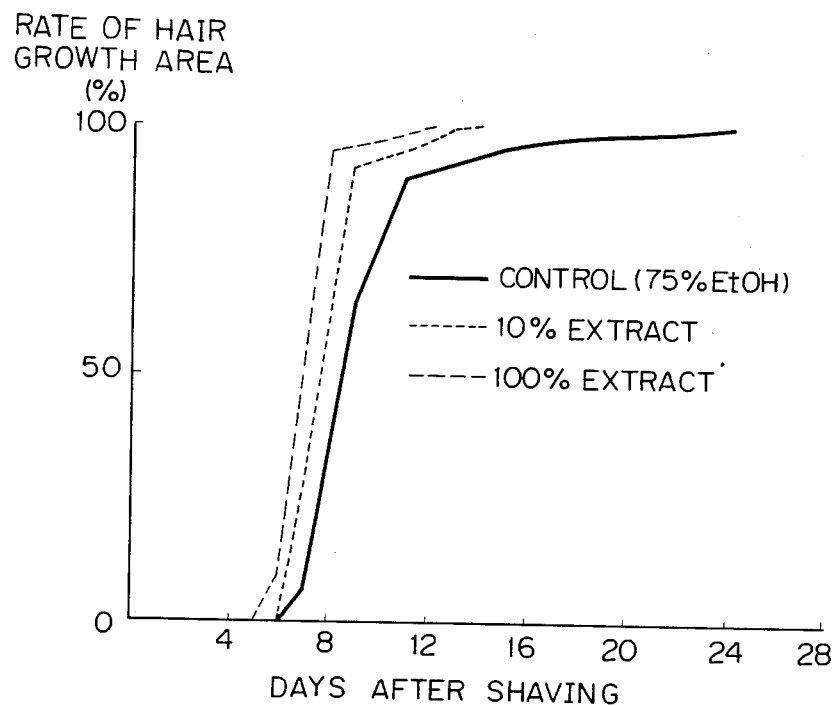

All groups consisted of ten mice per group. A mean value was calculated for each group from the result obtained from the mice. The results are shown in FIGS. 1, A and B. As seen from the Figure, samples containing over 1% of the original extract were especially effective for the regeneration of hair.

EXAMPLE 5

Figure 2A:
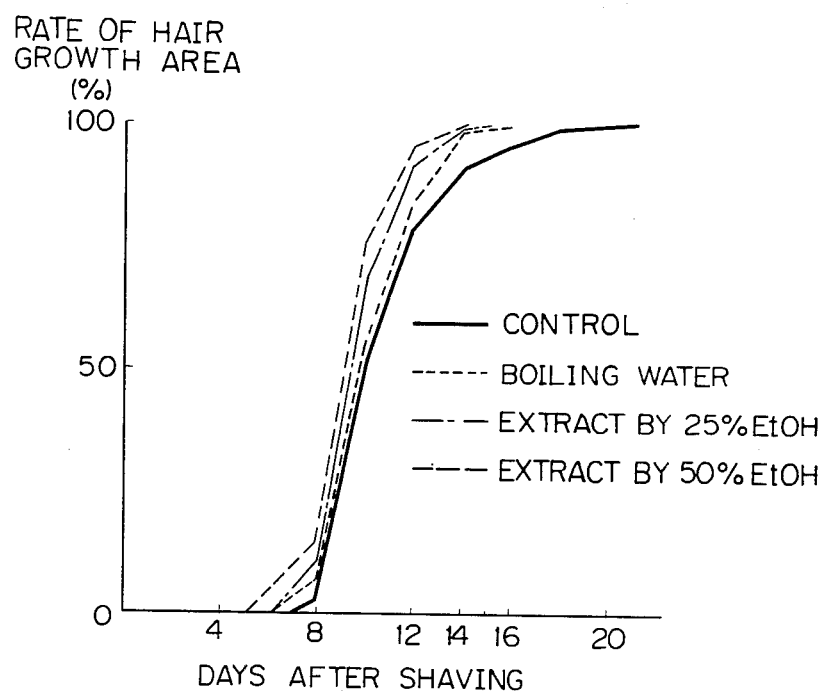
Figure 2B:
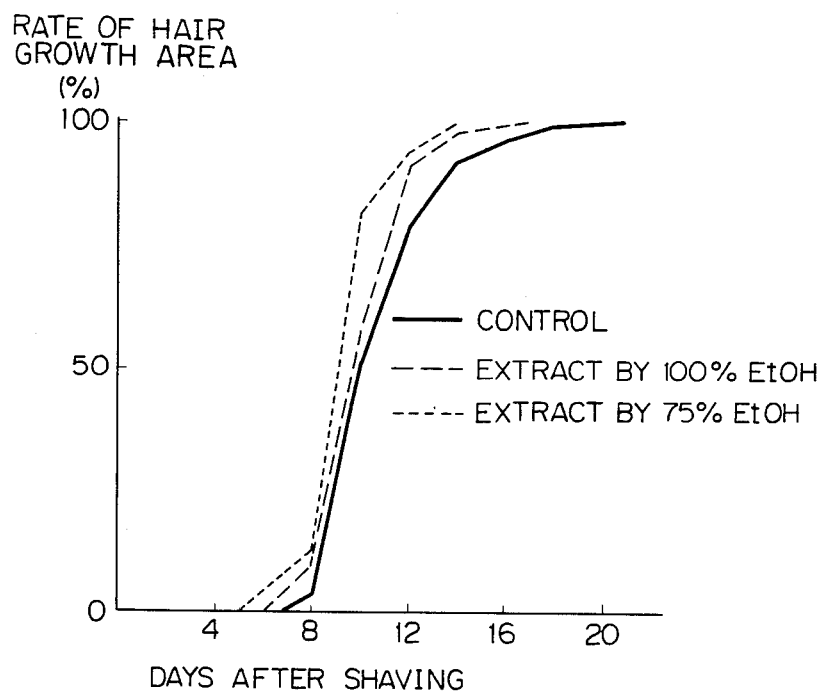

15 g each of dong chong xia cao was soaked in 200 ml each of 25%, 50%, 75%, or 100% ethanol, respectively, at a room temperature for 7 days, and the mixture was filtered to obtain an extract. And also 15 g of dong chong xia cao was added with 200 ml of distilled water, and the mixture was allowed to stand for 1 day and then refluxed for 4 hours. The mixture was filtered to obtain an extract. These extracts were tested according to the method described in Example 4. As shown in FIGS. 2, (A) to (B), when a mixture of ethanol and water is used as the extraction solvent, the concentration of the ethanol is preferably selected to be between 50% and 75%.

We claim:

1. A hair tonic composition comprising an effective amount of an extract extracted by a solvent from dong chong xia cao and a conventional base medium for hair tonic composition.

2. A hair tonic composition according to claim 1, wherein the amount of extract is 0.00001 to 30% by weight in dried form in relation to a total weight of the composition.

3. A hair tonic composition according to claim 1, wherein the solvent is selected from the group consisting of methanol, ethanol, butanol, acetone, diethyl ether, water, and a mixture thereof.

4. A method for preventing the generation of dandruff or scurf in hair or itching in the scalp comprising applying to the scalp the hair tonic composition of claim 1.

5. A process for production of a hair tonic composition of claim 1, comprising extracting dong chong xia cao with a solvent to obtain an extract, and combining the extract with a conventional base medium for hair tonic composition.

6. A process according to claim 5 further comprising the step of evaporating the extract to dryness before combining the extract with the base medium.

* * * * *